United States Patent
Uehara

(10) Patent No.: US 10,406,434 B1
(45) Date of Patent: Sep. 10, 2019

(54) VIDEO GAME CONTROLLER USING CORE MUSCLES AND OTHER APPLICATIONS

(71) Applicant: Alert Core, Inc., Kailua, HI (US)

(72) Inventor: Gregory Takeo Uehara, Kailua, HI (US)

(73) Assignee: Alert Core, Inc., Kailua, HI (US)

( * ) Notice: Subject to any disclaimer, the term of this patent is extended or adjusted under 35 U.S.C. 154(b) by 424 days.

(21) Appl. No.: 15/203,995

(22) Filed: Jul. 7, 2016

Related U.S. Application Data

(63) Continuation-in-part of application No. 15/164,681, filed on May 25, 2016, now Pat. No. 10,292,647, and a continuation-in-part of application No. 14/789,136, filed on Jul. 1, 2015, now Pat. No. 9,706,962, which is a continuation-in-part of application No. 14/132,808, filed on Dec. 18, 2013, now Pat. No. 9,226,706.

(60) Provisional application No. 62/189,812, filed on Jul. 8, 2015, provisional application No. 62/166,093, filed on May 25, 2015, provisional application No. 61/739,160, filed on Dec. 19, 2012, provisional application No. 62/019,522, filed on Jul. 1, 2014.

(51) Int. Cl.
*A63F 13/428* (2014.01)
*A63F 13/211* (2014.01)
*A63F 13/25* (2014.01)
*A63F 13/212* (2014.01)

(52) U.S. Cl.
CPC .......... *A63F 13/428* (2014.09); *A63F 13/211* (2014.09); *A63F 13/212* (2014.09); *A63F 13/25* (2014.09)

(58) Field of Classification Search
CPC .... A63F 13/428; A63F 13/211; A63F 13/212; A63F 13/25; G06F 19/3481; A61B 5/486; A61B 5/1107; A61B 5/1116; A61B 5/1121; A61B 5/7425; A61B 5/7435
See application file for complete search history.

(56) References Cited

U.S. PATENT DOCUMENTS

| | | | |
|---|---|---|---|
| 5,078,152 A * | 1/1992 | Bond | A61B 5/224 600/587 |
| 6,185,451 B1 * | 2/2001 | Richardson | A61B 5/0488 600/546 |
| 9,226,706 B2 * | 1/2016 | Uehara | A61B 5/227 |
| 2002/0143277 A1 * | 10/2002 | Wood | A61B 5/1071 600/595 |

(Continued)

*Primary Examiner* — Lisa M Caputo
*Assistant Examiner* — Philip L Cotey
(74) *Attorney, Agent, or Firm* — Staniford Tomita LLP

(57) ABSTRACT

A wearable device has a core contraction sensor and a movement sensor which transmits signals to a processor which analyzes the signals and uses the data to control aspects of a video game. The core contraction signal may determine if the user's core is contracted or relaxed. A video game may be used with the wearable device to encourage usage of the core muscles with the player getting points or rewards for engaging their core muscles and properly timing the engagement of the core muscles with body movements. The wearable device may be used in place of, or together with conventional video game control devices. Developing the habit of using the core muscles during may be beneficial in back pain rehab and prevention, fitness training and wellness, athletic performance improvement, and reducing workplace injuries in occupations involving heavy lifting.

20 Claims, 16 Drawing Sheets

(56) References Cited

U.S. PATENT DOCUMENTS

| | | | |
|---|---|---|---|
| 2008/0001735 A1* | 1/2008 | Tran | G06F 19/3418 340/539.22 |
| 2008/0234113 A1* | 9/2008 | Einav | A61B 5/103 482/66 |
| 2009/0270170 A1* | 10/2009 | Patton | A63F 13/10 463/36 |
| 2010/0240495 A1* | 9/2010 | Law | A63B 21/0004 482/9 |
| 2011/0269601 A1* | 11/2011 | Nelson | A47C 7/021 482/8 |
| 2011/0270135 A1* | 11/2011 | Dooley | A61B 5/1121 600/595 |
| 2012/0109399 A1* | 5/2012 | Tran | H02J 3/14 700/296 |
| 2012/0116256 A1* | 5/2012 | Stavdahl | A61B 5/04888 600/595 |
| 2012/0259648 A1* | 10/2012 | Mallon | G06F 19/3418 705/2 |
| 2014/0336947 A1* | 11/2014 | Walke | A61B 90/98 702/19 |
| 2015/0148708 A1* | 5/2015 | Cordo | A61B 5/1107 600/587 |
| 2016/0151000 A1* | 6/2016 | Shimuta | A61B 5/7207 600/484 |

* cited by examiner

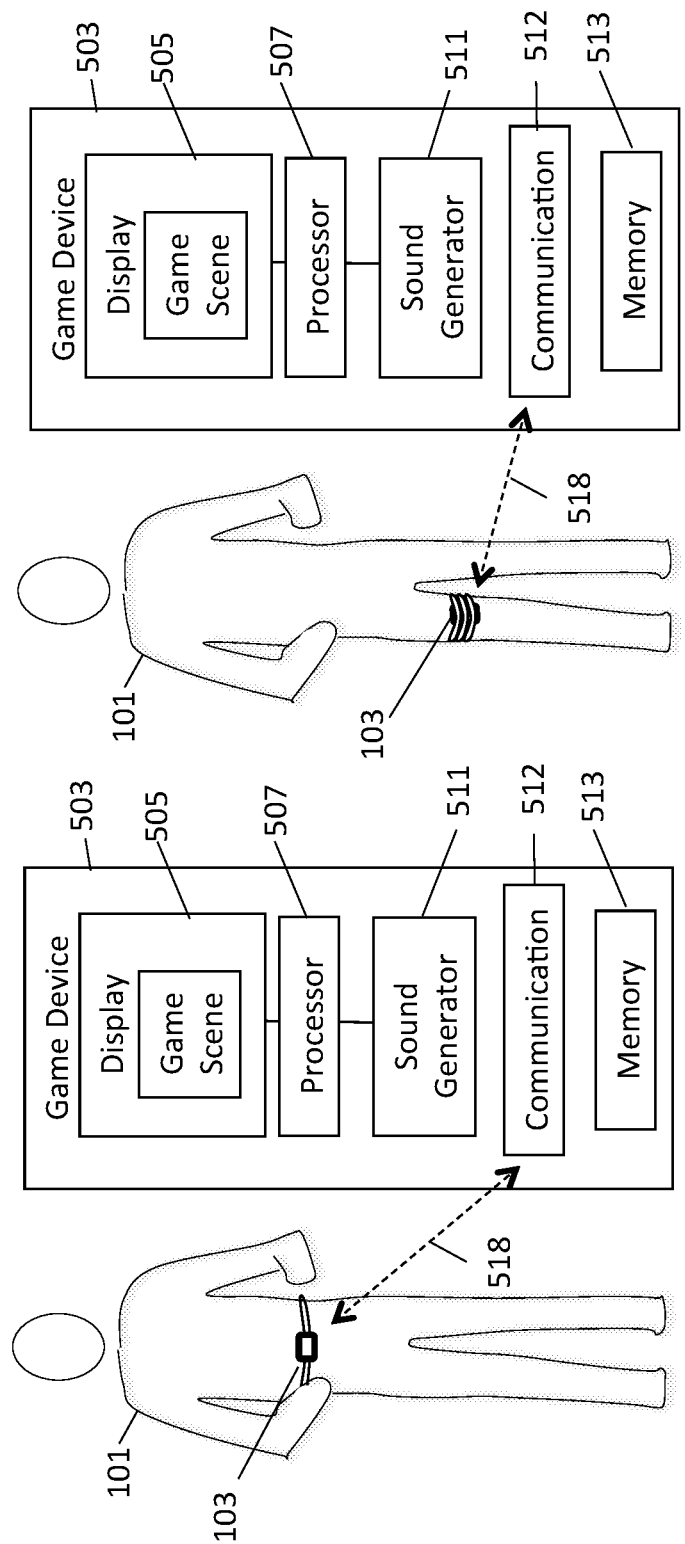

| Avatar | Game Challenge | Desired Player Movement | Sensor Signals | Video Feedback Signals | |
|---|---|---|---|---|---|
| | | | | Favorable (positive) with core properly contracted | Ramification (negative) with core improperly contracted |
| Race car | Avatar is racing opponent | Speed may increase when core engaged | Core contraction | Car may speed up | Car may move at slow speed |
| Shooting cannon | Avatar shooting objects | Cannon may be fired when core engaged (from relaxed) | Core contraction | Cannon may fire | Cannon may not fire |
| Base station under attack by cannon balls | Move protective shield into place to protect base station | Hip rotation may move shield in direction of incoming cannon balls | Core contraction and movement | Shield may move when rotation is Protected QM | Shield may not move when rotation is Unprotected QM |
| | Turn on shield prior to contact with cannon ball | Relax and then engage core with no body movement | Core contraction and movement | Shield may turn on | Shield may not turn on causing base station strike |
| Person running through obstacles | Avatar confronts low hanging beam from ceiling while moving forward | Engage core and bend down at knees | Core contraction and movement | Avatar may pass beneath beam (may require Protected QM) | Avatar may strike head on beam and get injured, or play may end |
| Person running through obstacles | Avatar confronts low wall while moving forward | Engage core and jump up gently | Core contraction and movement | Avatar may pass over wall (may require Protected QM) | Avatar may run into wall and get injured, or play may end |
| Flying hero | Avatar flies into drone | Engage core before and through impact | Core contraction and movement | Avatar may fly through drone (may require Protected QM) | Avatar may crash into drone then fall or get injured, or play may end |
| Swimming hero | Avatar swims into large buoy | Engage core before and through impact | Core contraction and movement | Avatar may swim through buoy (may require Protected QM) | Avatar may crash into buoy, sink, or get injured, or play may end |
| Injured avatar with number representing avatar strength (various games) | Avatar injuries accumulate toward termination (declining avatar strength number) | Perform Protected QMs to get strength points to reverse injuries | Core contraction and movement | Avatar strength number may be incremented | Avatar strength number may be decremented |

FIG. 5b

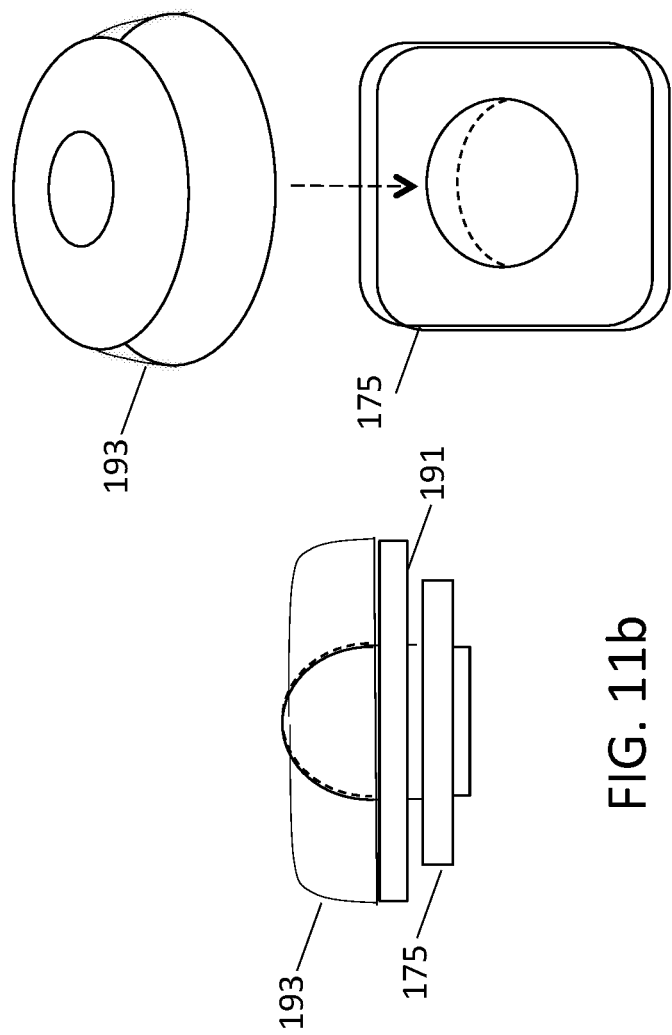
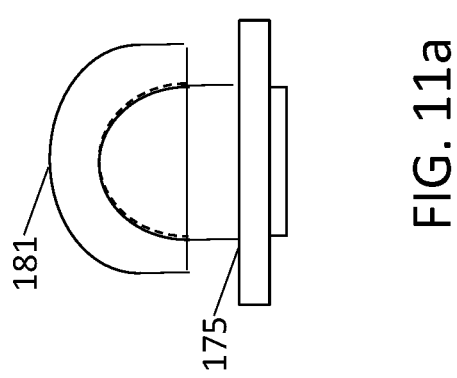
FIG. 11c
FIG. 11b
FIG. 11a

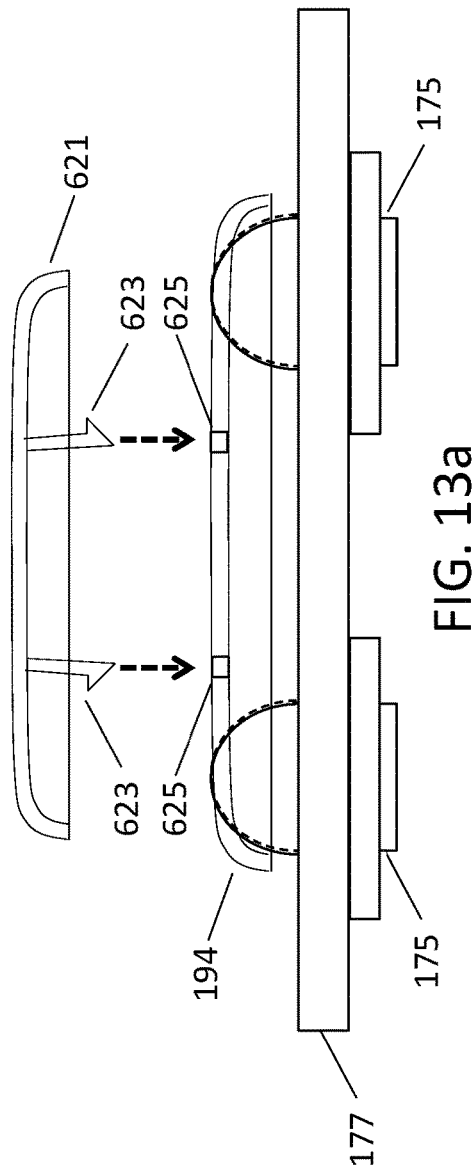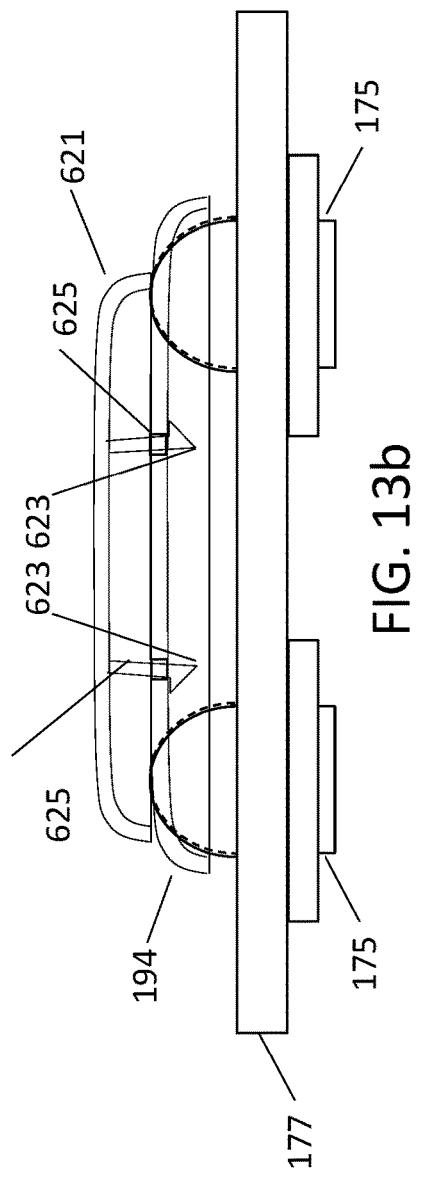
FIG. 13a
FIG. 13b

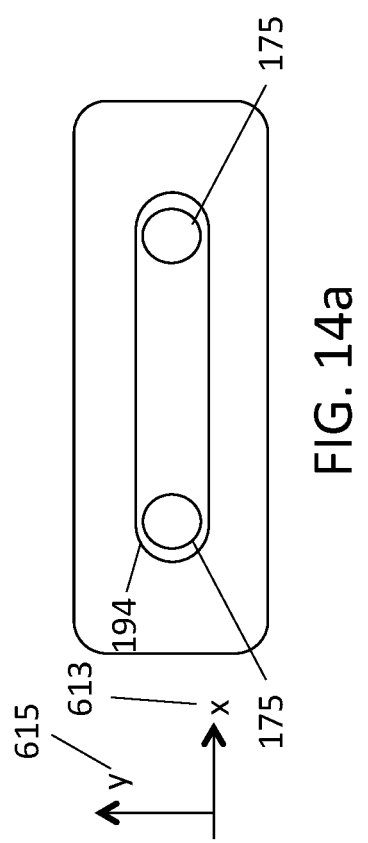
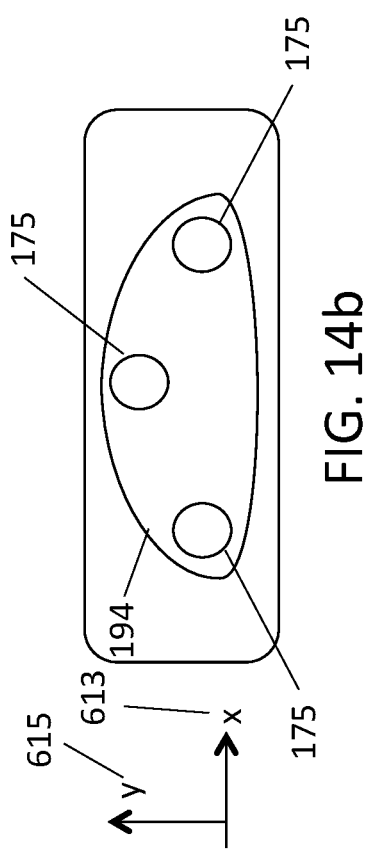

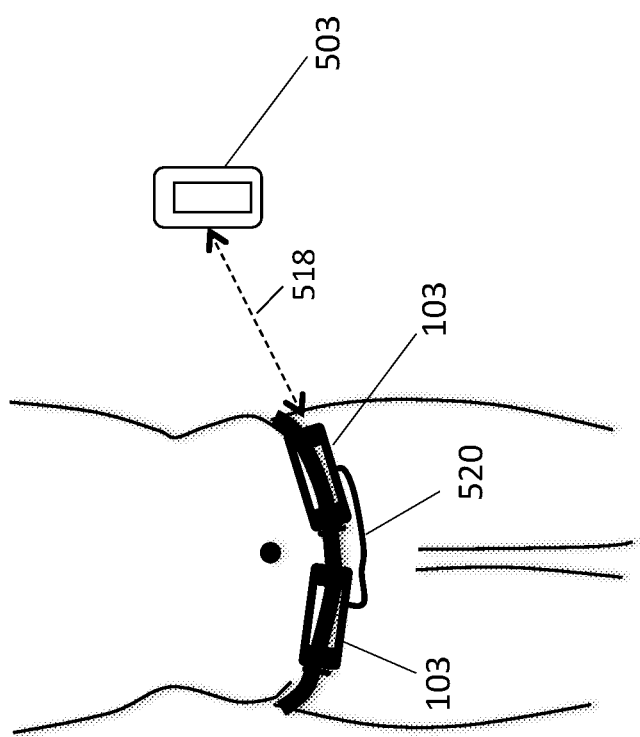

VIDEO GAME CONTROLLER USING CORE MUSCLES AND OTHER APPLICATIONS

CROSS-REFERENCE TO RELATED APPLICATIONS

This application claims priority to U.S. Provisional Patent Application No. 62/189,812, entitled "Video Game Controller Using Core Muscles", filed Jul. 8, 2015. This application is a continuation in part of U.S. patent application Ser. No. 15/164,681, entitled "System For Teaching And Improving Athletic Performance Utilizing Wearable Device Worn Over The Core Muscles", filed May 25, 2016 which claims priority to U.S. Provisional Patent Application No. 62/166,093, entitled "System For Teaching And Improving Athletic Performance Utilizing Wearable Device Worn Over The Core Muscles", filed May 25, 2015. This application is also a continuation in part of U.S. patent application Ser. No. 14/789,136, entitled "Apparatus And Method For Teaching And Algorithms For Identifying Qualifying Movements", filed Jul. 1, 2015, which is a continuation in part of U.S. patent application Ser. No. 14/132,808, entitled "System, Apparatus, And Method For Promoting Usage Of Core Muscles And Other Applications", filed Dec. 18, 2013, now U.S. Pat. No. 9,226,706 which claims priority to U.S. Provisional Application No. 61/739,160, entitled "System For Promoting Usage Of Core Muscles And Other Applications", filed Dec. 19, 2012. The disclosures of U.S. patent application Ser. Nos. 14/132,808, 14/652,542, 14/789,136, 14/817,964, 15/164,681, 61/739,160, 62/154,626, 62/166,093, and 62/189,812 are hereby incorporated herein by reference in their entirety.

FIELD OF THE INVENTION

Embodiments disclosed relate to apparatus, systems, and methods to encourage and develop use of the core muscles for low back pain therapy, rehab, and prevention, fitness training and wellness, and improving athletic performance by detecting core muscle usage and body movements using a wearable device and using the data in a user's control of a video game. Using data from the sensors to identify movements and core muscle engagements, feedback may be provided to the user regarding correct or incorrect core muscle use or preferred or unpreferred core muscle use. Embodiments disclosed may be applied to muscles in addition to the core muscles such as the vastus medialis oblique (VMO). Embodiments relate to a system including a wearable device that can identify user movements and contraction of the user's core muscles, and combine user movement and core muscle data to control an avatar, objects, or other items in or aspects of a video game as part of a system to encourage the development of core muscle usage.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be embodiments of the invention.

In recent years, there has been explosive growth in the number of portable and handheld devices that include sensors such as accelerometers, gyros, magnetometers, altimeters, and/or pressure sensors. Examples of such devices include smart phones, cell phones, gaming devices, and wearable devices (or wearables). In video game devices, tilt or angles of rotation are often tracked and used to control elements of the game. A large number of wearables target health and fitness applications where steps taken and flights of stairs taken by device users are tracked utilizing accelerometers and altimeters.

Inertial navigation is a method utilizing accelerometers, gyroscopes or gyros, and a microprocessor contained on a moving object to continuously calculate device positions utilizing dead reckoning the position, orientation, and velocity of the object. Dead reckoning is the process of calculating the current position by using a previously determined position and advancing that position based on estimated speeds over known elapsed time. A system implementing inertial navigation is self-contained and requires no external references. Inertial navigation has generally been used by aircraft, spacecraft, guided missiles, and ocean craft. Inertial navigation may be used in embodiments of the inventive concepts described in this disclosure targeting systems and devices for the wearables market.

Most health and fitness wearables on the market today may track one or more of the following: steps taken, number of stairs taken, heart rate, movement activity, and sleep patterns. These devices generally utilize accelerometers, altimeters, light sources and sensors, and voltage sensors to sense and detect the parameters they measure and track.

Back injuries are a common problem. Core muscle based support can be used as a means for supporting the lumbar spine and preventing back injuries. While there has been much attention in exercise and rehabilitation environments to strengthening the core muscles through various exercises, very little emphasis has been placed on developing the habit for deliberate contraction and use of the core muscles in every day activities. What is needed for exercise and rehab, as well as for general wellness is a system and method for improving core muscle based support through core muscle exercise and the practice of core muscle usage during body movements. Such a system and method may encourage users to develop neural patterning to contract core muscles deliberately when the support provided by the core muscles may be beneficial. This system and method may further develop neural patterning to coordinate the contraction of the core muscles before and during body movements.

SUMMARY OF THE INVENTION

In U.S. Pat. No. 9,226,706, entitled "System, Apparatus, And Method For Promoting Usage Of Core Muscles And Other Applications", an inventive system is presented including a wearable device which monitors a user's movements for Qualifying Movements (QM), where a QM is a movement for which support from contraction of the core muscles may be beneficial to the lumbosacral junction and lumbar spine. When a QM is identified, the system determines whether or not the QM is protected or not protected based on the status of the user's core before, during, and after the QM. Objectives of the system include: having the user contract their core muscles during the time the stress on the lumbar spine and lumbosacral junction is greatest during a QM; and having the user develop the habit of contracting their core muscles during QMs such that they continue this beneficial practice even without the system. In general, if the core is contracted before and during the QM, the QM may be considered protected. However, since it is protecting the lumbosacral junction and lumbar spine when the stress is greatest that matters most, having the core contracted during periods when, for example, the acceleration or deceleration is greater than a threshold may also result in a QM being considered protected. An overall objective of the system is to provide a system and method for developing core muscle usage employing video games utilizing data from the wearable device. The use of video games may be used to encourage a user to practice core muscle usage more regularly and for longer periods of time than they may otherwise.

The wearable device and app described in U.S. Pat. No. 9,226,706 has been described to develop usage of the core muscles. The wearable and app may also be used to monitor other muscles and other body movements. For example, after a knee surgery, the Vastus Medialis Oblique (VMO) muscle in the thigh will tend to atrophy. The described device may be used in a modified strap that is then placed over the VMO. The core contraction sensor becomes a muscle contraction sensor where in this case, the muscle is the VMO. The present description will focus mainly on development of the core muscles. However, the inventive concepts described here and in the descriptions incorporated by reference may be applied to the development and training of other muscles. The VMO is one such example muscle.

Video games are prevalent in our society. In addition to dedicated video game equipment, video games exist on just about all consumer electronic devices containing a display including cell phones, smart pads, smart watches and personal computers. There are many reasons for the ubiquity of video games, some of the reasons may include: they allow the user to pass time while waiting; there is the aspect of the challenge that allows a user to compete with themselves or with others, thus encouraging practice in order to improve performance or skill; they are entertaining; they can be educational; and they may be combinations of two or more such reasons. By combining video games with a device that monitors core muscle usage and body movement, the connection from the brain to the core muscles may be strengthened and the habit of engaging the core muscles with body movements may be encouraged. Since the device that monitors core muscle usage may also be used to monitor the contraction of other muscles, video games may be used to encourage the use of other muscles as well. The combination of the video game and wearable device may be used in in many applications such as therapy, rehab, fitness training, athletic training, wellness, and pain prevention.

In an embodiment, data from the core sensor and movement sensor are used to evaluate Movement Criteria. The user or player of the video game may encounter a Ramification if Movement Criteria is not met, or a Favorable Outcome or simply a Favorable if Movement Criteria is met. In an embodiment, a Protected Qualifying Movement meets the requirements of Movement Criteria. In an embodiment, a Ramification is that an avatar does not move in response to a movement or movement combination by the player that does not meet the Movement Criteria. In another embodiment, a Ramification results in a negative value being added to a score in response to a movement or movement combination that does not meet Movement Criteria. In an embodiment, a Favorable is that an avatar moves in an expected manner in response to a movement or movement combination that meets Movement Criteria. In another embodiment, a Favorable results in a positive value being added to a score in response to a movement or movement combination that meets Movement Criteria.

In an embodiment, the system disclosed may use data from the core sensor and movement sensor to determine when the core muscles are engaged and the direction or orientation and speed of body movements, and this data may be used to control a parameter or parameters of or an avatar in video game.

In an embodiment, the video game may simply repetitively encourage engaging and relaxing the core muscles. In an embodiment, the video game may additionally encourage engaging the core muscles in combination with other body movements.

In an embodiment, the video game may run locally on a smart device, computer, or other dedicated device and be have game features that encourage specific behaviors such as contracting the core muscles before and through movements.

In an embodiment, the video game program may convert core contraction signals into core contraction video feedback signals that are output to a display wherein the video feedback signals may include actions to or involving an avatar depending on the core contraction signals.

In an embodiment, the video game program may convert core contraction signals and movement signals into qualifying movement video feedback signals that are output to a display wherein the video feedback signals may include actions to or involving an avatar depending on the timing relationship between the core contraction and movement signals.

In an embodiment, the data from the core sensor and movement sensor may be used as control parameters for a dedicated video game optimized for the wearable device and designed to encourage core muscle usage.

In an embodiment, the data from the core sensor and movement sensor may be input to a translator that couples to a game controller, where the translator converts parameters from the core sensor and movement sensor into parameters to control the video game. This may enable the core sensor and movement sensor to be used as input parameters for any video game.

In an embodiment, an Application Program Interface may be defined for the data from the wearable device to enable game developers to write games to interface with the wearable device. In an embodiment, the wearable device may be used with this Application Program Interface to provide user inputs to an online game where the code for the game is run on a server and video data is sent back to a local display for viewing by the player.

In an embodiment, a game system that utilizes signal processing on camera video to generate an estimate of a real-time 3-D model of the player's position and movements combined with data from the wearable device monitoring the player's core contraction and sensed body movements in order to provide feedback through the video game, enabling the player to develop improved and habitual coordination of core contraction with body movements via at-home play and practice.

In an embodiment, two wearable devices may be used to monitor a user's core muscles in different locations. The two wearable devices may be connected via a wired communication link while one of the devices may connected to a smart device via a wireless communication link. This may allow data from two wearable devices to communicate to an app simultaneously.

In an embodiment, two or more bumpers coupling to two more force sensors or pressure sensors or two or more sections of a force sensor are utilized. This may result in a larger sensing area for coupling to the core muscles. In an embodiment, another element may be placed over the two or more bumpers further increasing the sensing area. In an embodiment, the additional element may be designed to maximize coupling from the muscles to the additional element, that is then coupled to the bumpers, and finally coupled to the sensors, while eliminating or minimizing direct contact between the additional element and the face of the wearable device.

In an embodiment, parameters of the wearable device, strap, or belt may be modified to place the device over a muscle in addition to the core muscles in order to develop that muscle. In an embodiment, the system may be utilized to develop usage of the VMO.

A comprehensive system to teach users to contract their core muscles during athletic, fitness and strength training, and rehab may be beneficial to users as well as coaches, therapists, trainers, and others teaching the development of the sequenced core to athletes, clients, and patients. Such a system may be comprised of a variety of elements to support establishment of the brain to core muscle connection, to develop at-will use of the core muscles, and to practice and develop the habit of using core muscle contraction in coordination with other body movements. In addition to providing simple biofeedback, such a system may benefit from a protocol of exercises and entertaining ways to practice the use of the core muscles. The incorporation of video games in the development and practice of muscle use is one such method to make such practice of the use of core muscles entertaining for the user.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

FIG. 4a illustrates an embodiment of the wearable device worn over a player's core muscles to provide player control to a video game.

FIG. 4b illustrates an embodiment of the wearable device worn over a player's right VMO to provide player control to a video game.

FIG. 5b includes a table containing examples of avatars, game challenges confronted by a player, desired physical movement of a player upon the challenge, sensor signals used and corresponding sensor video feedback.

FIG. 11a illustrates an embodiment of a bumper with an extender cap.

FIGS. 11b and 11c illustrate an embodiment of an extender cap that increases the girth but not the height of the bumper.

FIGS. 13a and 13b illustrate an embodiment of a unifier cap extender connecting to a unifier cap over a two bumper implementation.

FIG. 14a illustrates a top view looking into the face of the device of a two bumper design with an embodiment of a unifier cap.

FIG. 14b illustrates a top view looking into the face of the device of a three bumper design with an embodiment of a unifier cap.

FIG. 15 illustrates a two-wearable device configuration with communication link to a smart device.

DETAILED DESCRIPTION

Figure 1:
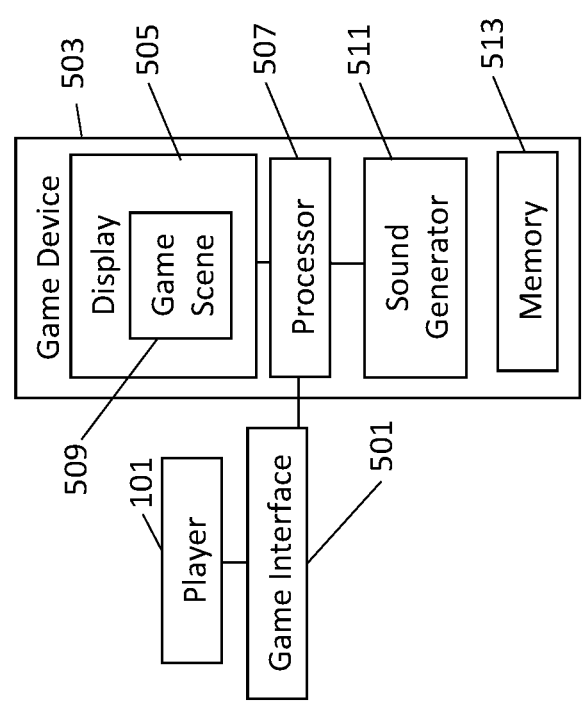
FIG. 1 illustrates a prior art diagram of a player, game interface, and game device running a video game.

In U.S. Pat. No. 9,226,706, an inventive device and system is described, one embodiment of which enables real-time tracking of the core muscles by tracking core muscle contraction with a core contraction sensor and body movements with a movement sensor. The inventive device and system encourage the development of procedural memory for usage of the core muscles. The core contractions can then be used during Qualifying Movements (QMs) which are defined as movements for which contraction of the core muscles may be beneficial in supporting the lumbosacral junction and lumbar spine. In an application, when a QM is identified by the system, the system determines whether or not the QM is protected or not protected based on the status of the user's core before, during, and after the QM. The wearable device and system may be used to develop a sequenced core, that is core muscle engagement that is deliberate and coordinated with other body movements.

In this current description, an inventive system is described to utilize the wearable device as an input controller to video games for the purpose of encouraging and teaching a user-player of the video game system to use their core muscles more effectively and in a coordinated manner with movements of their body. The system may also be beneficially used for teaching preferred ways to perform specific movements that may have benefit for reducing stress on the spine and other parts of the body.

There are a wide variety of controllers used to control athletic equipment, avatars, weapons, vehicles, people and other objects in video games today. Joysticks were used predominantly in the early days of video games back in the 1970's and they are still widely used today. Moving an object or avatar left or right in one-dimensional control; left, right, forward, backward, and in combination for two-dimensional control is what a joystick has been used for since the early days of video gaming. With an additional joystick, the control of up and down can be added to the two-dimensional controller for control in three-dimensions.

Recently introduced video game platforms such as Xbox Kinect by Microsoft Corporation have popularized video sensing where the body movements of a player are tracked and used to control avatars or other objects. The Microsoft Corporation Xbox Kinect uses video images and an infrared sensor to resolve distance allowing it to identify and track body movements and body positioning. Players simply stand in front of the specialized camera, move their bodies, and their movements are converted to data that can be used to control an avatar or other object in a video game. The Sony Playstation Move Controller uses a wand-like device that may be moved in 3-D space by a player's hand and the movements are tracked using inertial navigation with sensors including accelerometers, gyros, and a magnetometer. The sensor movements are then sent wirelessly to a controller box which converts the player's movements into the movement of an avatar or other objects in a video game. The use of inertial navigation using low-cost sensors has become widely used in video gaming.

User body movements for controlling an avatar or object in a video game has brought on a new generation of games and ways of playing and interacting with games. Players are able to get exercise with the controllers that utilize body movements. 3-D glasses are enabling yet another approach to present video games to players. 3-D glasses in video gaming is still being improved but promises to allow players to interact with game environments in new and even more lifelike ways.

Video games are generally played by players for entertainment. Some games provide additional utility by encouraging players to perform body movements resulting in players receiving the benefit of exercise. Some of these games are used in physical therapy to encourage patients to move in specific and beneficial ways.

The inventive system described in U.S. Pat. No. 9,226,706 enables real time tracking of the inner core muscles. Furthermore, it encourages the development of procedural memory for support of a user's lumbosacral junction and lumbar spine by encouraging a user to contract their core muscles before and during performing Qualifying Movements.

There are no games available today that encourage a player of a video game to deliberately contract their core muscles before or in combination with body movements as a training or development tool for improved health and usage of core muscles. This current invention brings the motivational and entertainment value of video games into the learning process of using the core muscles more effectively. Different timing models of core contraction and body movements may be encouraged. For example, a user or player of the game may be encouraged to contract their core before and during movements, during movements, and before, during and after movements. Players may be encouraged to contract their core for some movements and not others. The preferred contraction patterns may also be conditional, depending on the magnitude of a movement or the speed of the movement. In the following, the terms user and player will be used interchangeably.

A user may be encouraged to use their core in conjunction with specific movements by receiving points for performing certain combinations of core contraction and movements and by not receiving points for performing certain combinations of core contraction and movements. The avatar or object under control may move when the core is contracted during a movement of the player's body and not move when the player's core is not contracted in a specific preferred way. For example, an object in a video game may move to the right when a standing user slides to their right or the object may move to the left when a standing user slides to their left only when the player contracts their core prior to sliding to the right or left throughout the duration of the slide. In another embodiment, the object may slide if the player contracts their core during a substantial portion of the duration of the slide. Timing requirements of the core contraction in relation to a movement of a player's body enabling movement of an object in a video game may be modified in software. The magnitude that the object in the video game moves to the left or right may be substantially proportional to the distance that the player slides to the left or right with their core appropriately contracted.

The concepts presented describe using body movements of a user wearing the wearable device converted to similar movements of an avatar or object in a video game when the user's core is contracted appropriately. This concept is very general and may be applied to many types of video games. The invention can be beneficial to most users who want to learn to more effectively utilize their core muscles. The invention may also be beneficial for those in therapy for back pain. Video game content, player movements and core usage may be designed for therapeutic and rehabilitation applications, as well as building muscle memory or neural patterning for core usage in health and fitness, wellness, athletic performance improvement, and workplace injury reduction.

Referring to FIG. 1, a block representation of a typical video game system is shown. The user or game player 101 interacts with the video game by controlling Game Interface 501. Examples of Game Interface 501 include joysticks; embedded sensors in state-of-the-art smart phones, smart pads, and smart watches; steering wheels; flight controllers; guns; music instrument emulators; computer keyboards; computer touch pads; computer mice; foot pedals; and proprietary controllers such as Microsoft Corporation's Xbox Kinect sensor camera and the Sony PlayStation Move Motion Controller. Game Interface 501 converts movements of the user or player 101 into signals that are processed by Processor 507 and used to control an avatar or an element in a Game Scene 509 shown on a Display 505. Sound Generator 511 generates and drives audio signals through a speaker or headphone system. The Game Device 503 may include a display 505, processor 507, Sound Generator 511, and Memory 513. Memory 513 may include storage for storing programs for different games. It may also include memory that is used by the processor during the execution of program code to execute a game.

The game device 503 may be a PC or processor-based controller with a built-in or external monitor, smart phone or other handheld or countertop device containing a processor and a display. The display 505 may show an avatar or object that moves in response to the signal received from the Movement Sensing Device 501 in response to user 101 movements. In some video games, the surroundings of the avatar or object move relative to a stationary avatar or object creating the illusion that the avatar or object is moving. Processor 507 communicates with movement sensing device 501 and runs the software to execute the game. Communication blocks exist on both the Game Interface 501 and Game Device 503 but are not shown explicitly. These communication blocks may be wired or wireless.

Figure 2:
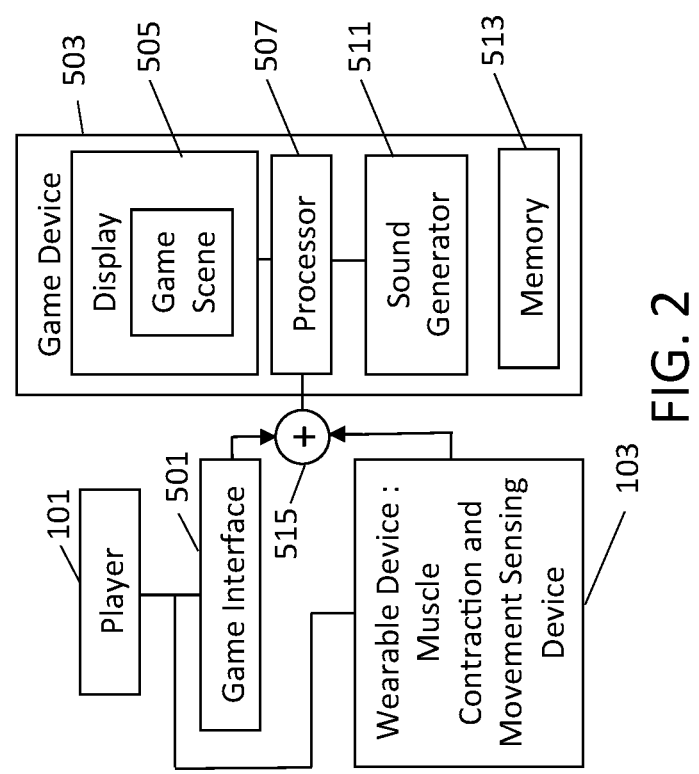
FIG. 2 illustrates an embodiment of a player attached to a game interface and wearable device where data from the game interface and wearable device is combined to create a player's control of the video game.

An embodiment of the inventive system is shown in FIG. 2. Player 101 has attached the wearable device 103. Data from the wearable device 103 may be combined with data from Game Interface 501 by data combiner 515 to form composite data that communicates with processor 507 which is part of Game Device 503. In an embodiment, data combiner 515 is implemented in Game Device 503. Communication blocks may be present in Game Interface 501, wearable device 103, and Game Device 503 and are not shown explicitly. These communication blocks may be wired or wireless. In an embodiment, wearable device 103 communicates to Game Device 503 via a wireless link and Game Interface 501 communicates with Game Device 503 via a wired link. In another embodiment, both wearable device 103 and Game Interface 501 communicate with Game Device 503 over a wireless link.

The addition of wearable device 103 may enable new learning features in video games. Core contraction sensor data and movement sensor data from the wearable 103 may be converted to video signals. In some embodiments, video signals may include video game scenarios that may be devised to encourage or elicit specific physical responses or actions by a player. The player may be encouraged to respond with certain movements or combinations of movements including appropriately timed core contractions. The core contraction sensor on the wearable 103 may be utilized to combine core contraction and core contraction timing with body movements in the video game. Some aspects of conventional Game Interface 501 may be utilized for control data in the video game. In some applications, only data from the wearable device 103 may be used. In other applications, data from the core contraction sensors on the wearable device 103 may be used with data from the Game Interface 501. In other applications, data from the movement sensors on the wearable device 103 may be used with data from the Game Interface 501.

In some applications, video game software may be written specifically to encourage core muscle usage and the development of a sequenced core. In such specific video games, the games may be written exclusively for wearable device 103. In these specific video games, wearable device 103 may be the exclusive source of player 101 control data or provide partial control data that may be combined with Game Interface 501 control data. These specific video games may emphasize core contractions and timing core contractions with body movements.

In other applications, the wearable device may be used partially or exclusively as the Game Interface 501 to games that were not written specifically for wearable device 103. In such non-specific video game applications, an Application Program Interface (API) may be utilized. An API is a set of tools for building software applications and may facilitate interfacing wearable device 103 with non-specific video games. An API may facilitate the development of a software driver that may run on processor 507 to translate player 101 actions detected by the wearable device 103 sensors into commands for the non-specific video games. At a basic level of abstraction, the core contraction sensor may for example send out data to the system informing when the player's 101 core muscles transition firstly from relaxed to engaged, and secondly from engaged to relaxed. This may be defined in an API for the wearable device 103 to facilitate interfacing the wearable device 103 to non-specific video games. In an embodiment where a non-specific video game is designed to perform a function upon a mouse click, a software driver may be used to perform the function when wearable device 103 detects a transition from a relaxed to engaged core. The API may also be used to facilitate enabling any programmer to write a specific video game software to work with the wearable device 103.

Figure 3:
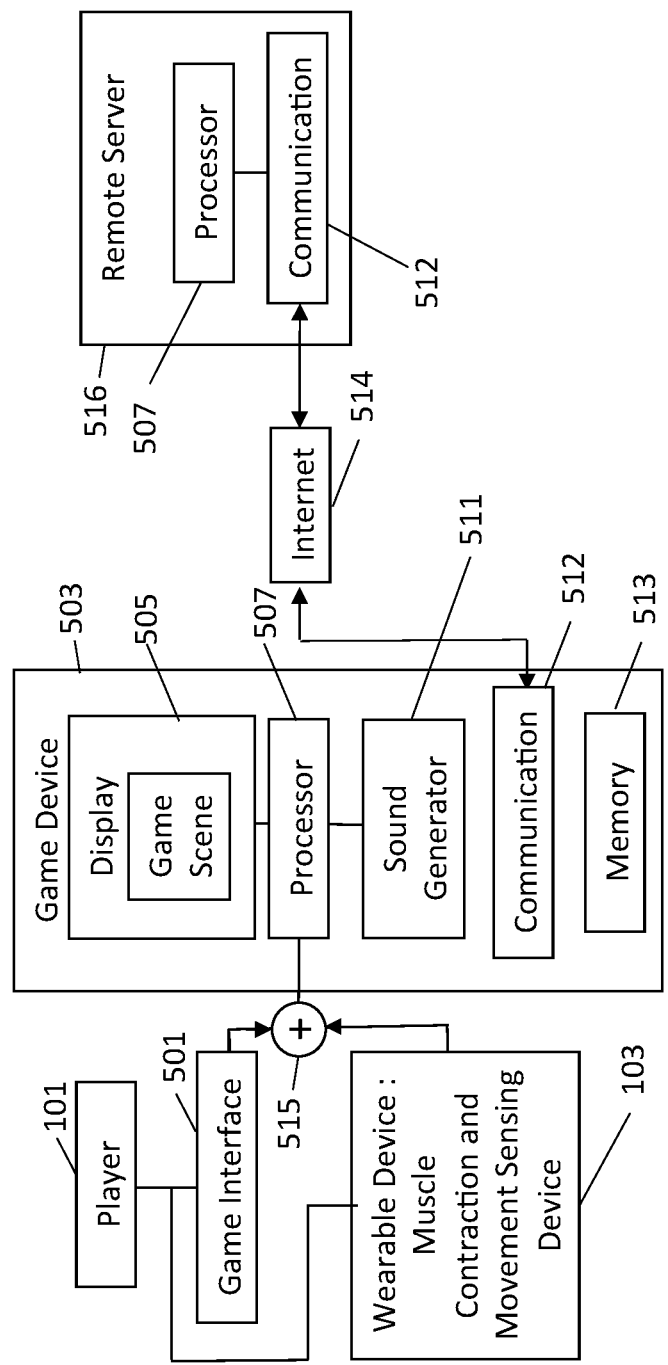
FIG. 3 illustrates an embodiment including a game interface and wearable device wherein the game software is run on a remote server and the display is shown on a device local to the player.

An embodiment of the inventive system is shown in FIG. 3 where the program code for the video game is run on a processor 507 on a remote server 516. Cloud gaming is an example of this system configuration. The player 101 may wear the wearable device 103 and interact with the Game Interface 501. The output of the wearable device 103 and Game Interface 501 may be combined and used as player data for the video game. This player data may be sent over communication block 512 in the Game Device 503 over the Internet 514 to the remote server 516. The video game program code may be run on a processor 507 on the remote server 516, and video and sound data may be sent back in real-time from the communication block 512 on the remote server 516, over the Internet 514, and to the communication block 512 on the game device 503. The processor 507 on the game device 503 may convert the video data into a video signal for display 505. The processor 507 on the game device 503 may convert the audio data into an audio signal and the audio signal may be output via a sound generator 511 on the game device 503. This configuration where the game is run on a remote processor may make an assortment of video games very accessible to users.

With reference to FIG. 4*a*, a player 101 is shown with wearable device 103 worn over the core muscles. Wearable device 103 communicates with communication block 512 on the game device 503. In an embodiment, wearable device 103 communicates with game device 503 over wireless link 518. In FIG. 4*b*, a player 101 is shown with wearable device 103 worn over the right VMO. Wearable device 103 communicates with communication block 512 on the game device 503. In an embodiment, wearable device 103 communicates with game device 503 over wireless link 518. FIGS. 4*a* and 4*b* illustrate the player 101, wearable device 103, and game device 503 in simple embodiments.

The wearable device 103 may be used to control a video game in different ways. In one embodiment called Movement Criteria Mode, Movement Criteria are evaluated for each movement using body movement sensor data and core contraction sensor data. In an embodiment, the timing relationship between core contraction and body movements and other parameters of the movement data may be evaluated against Movement Criteria. If Movement Criteria are met, the player's movement may be translated into something favorable in the video game. If Movement Criteria are not met, the player's movement may result in no movement or something unfavorable in the video game.

In another embodiment, the wearable device 103 provides additional player 101 control data directly, without evaluating timing relationships between the contraction sensor data and the movement sensor data. This is called Direct Movement Mode and data from the wearable device 103 may add to or replace the Game Interface to allow the player 101 to interact with the video game via the wearable device 103.

In Direct Movement Mode, as the player 101 moves their body, the wearable 103 will move. The movements may be detected by the movement sensor and translated into position changes in three dimensions. Depending on the avatar or object being controlled in the video game, this may be translated on the display as an equivalent change of the avatar or object in one, two, or three dimensions. The change in position may be proportional or non-linear, depending on the application. In a proportional change, if the player 101 moves to the right by one inch, the avatar or object may move equivalently to the right by one unit of distance. If the player 101 moves to the right by two inches, the avatar or object will move equivalently to the right by approximately two units of distance. In a non-linear change in position of the avatar or object, if the player 101 moves to the right by two inches, the avatar or object may move equivalently to the right by substantially less than two units of distance, for example one-and-a-half units of distance, or substantially more than two units of distance, for example three units of distance.

Figure 5A:
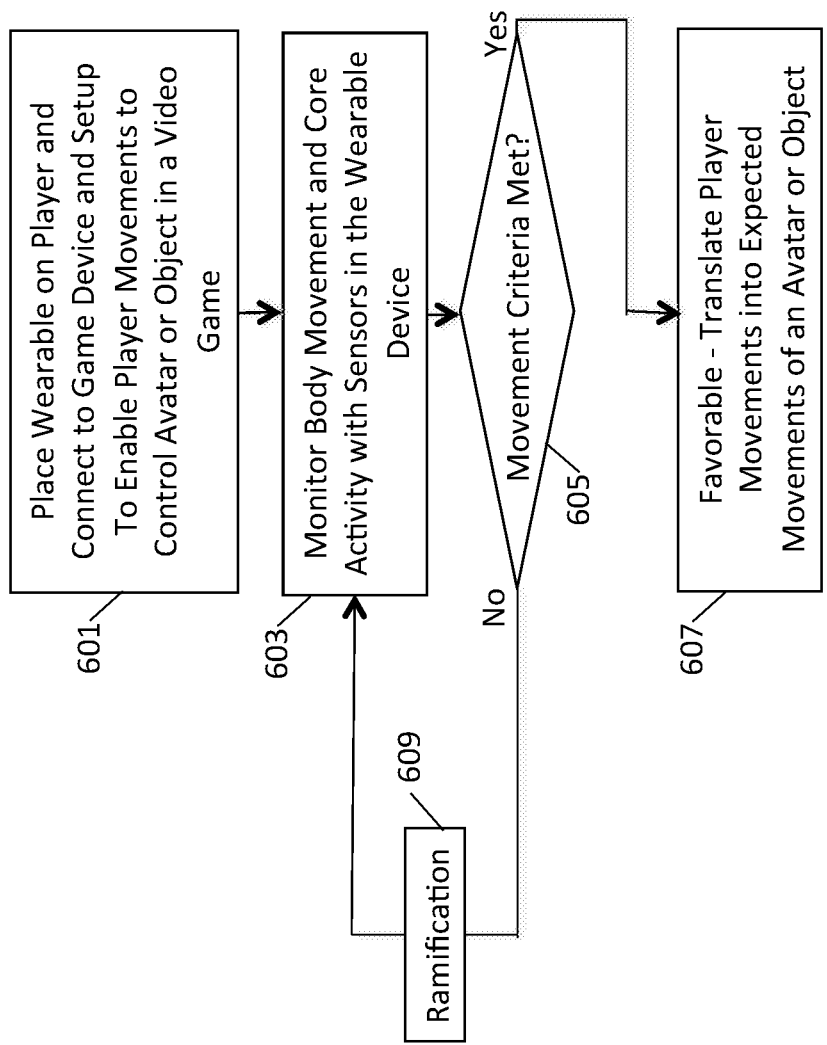
FIG. 5a illustrates a flow diagram for a game configuration utilizing Movement Criteria.

A flow diagram of Movement Criteria Mode is shown in FIG. 5. Begin by placing the wearable 103 on the player 101 and set up the system to enable the player movements to control an avatar or object in a video game 601. Next, monitor the player's 101 body movements and core contraction activity with the sensors on the wearable device 603. Movement Criteria are additional qualifications that may be placed on how and when the user contracts their core in relation to how they move. Example of Movement Criteria will be provided shortly. The next step in the flow diagram is to check whether or not Movement Criteria are met by the current user movement 605. If the Movement Criteria test 605 is not met, Ramification or Ramifications 609 result. This will have a detrimental effect on the users score or performance in the game. Examples of Ramifications 609 will be provided shortly. Finally, if the Movement Criteria test 605 are met, then the player's movements are translated into a Favorable 607 result, for example it may result in expected movements of the avatar or object, or points added to a player's 101 score.

Examples of Movement Criteria which may be combined or used in isolation depending on the application include but are not limited to:

A. The user must move from one position to a second position, and pause for a minimum duration of time, for example 250 msec before moving to a third position;

B. The discrete movements in A with pauses in between must be appropriately protected with contraction of the core muscles prior to the movements;

C. Only protected qualifying movements move the avatar or object correctly; or

D. Protected qualifying movements may require the core contraction begin before and throughout the entire movement;

The parameters and content of Movement Criteria tests 605 may be modified based on a number of factors. Examples of factors that may change or adjust Movement Criteria include a player's performance during a game or series of games, a player's pain condition, and a player's skill level in using their core muscles.

When one or more Movement Criteria are not met by a player's 101 body movements and core contraction during a movement during a game, a Ramification 609 may occur. A number of Ramifications 609 are possible. Ramifications 609 may occur in isolation or in combination. Examples of Ramifications 609 include no movement of the avatar or object in response to the movement of the player, partial or incorrect movement of the avatar or object in response to the movement of the player, negative points added to the player's score, demerits added to the player's score, or modifications to the content or parameters of the Movement Criteria.

In some embodiments, the data from the wearable device 103 may be converted to video signals that are output on a video display wherein the video signals include game scenarios, player movements, and Favorables and Ramifications in numerous and varied ways. A few such embodiments are shown in the table of FIG. 5*b*. The avatar column 602 describes the embodiment of the avatar. The game challenge column 604 describes a challenging scenario that the avatar may be confronted with in the course of the video game. The desired player movement column 606 describes the movement including core contraction that the player must perform in order to get a favorable response to the avatar. The sensor signals column 608 includes the sensor or sensors that may be used to determine video feedback signals 610. Video feedback signals 610 contains two columns. The favorable column 608 describes a favorable action to the avatar in response to the player performing the desired player movement 606. The ramification column 610 describes a negative action to the avatar in response to the player not performing the desired player movement 606. For example, in the first row, the avatar 602 is a race car. The game challenge 604 may be to race on a course with at least one other race car. The desired player movement 606 may be for the player to engage their core muscles. The sensor used 608 may be the core contraction sensor. Based on the core contraction signal, a core contraction video feedback signal 610 that may be output on a video display may be favorable 612 and the race car speed may increase or a ramification 614, wherein the race car speed may be a slow speed.

An avatar may include blocks, squares, rectangles, balls, circles, triangles, food objects, animals, plants, insects, fantasy objects like magic wands or unicorns, or other objects. This table is an example of a video game objective, a player's required movement to achieve the objective, and the results of the player performing the movement correctly or incorrectly. Many applications and game scenarios are possible.

Figure 6:
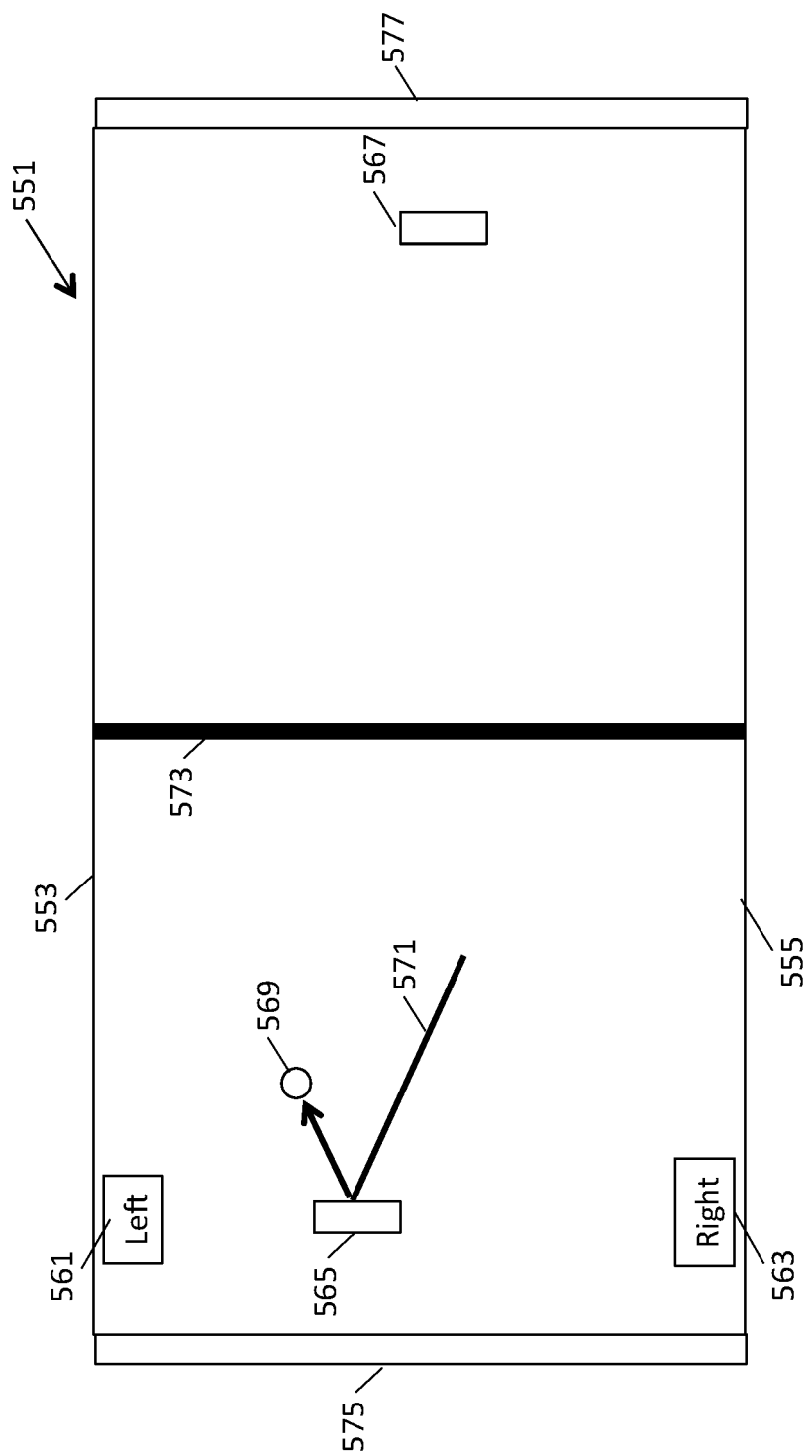
FIG. 6 illustrates an embodiment of a ping pong game display.

An example of a ping pong game is illustrated in FIG. 6. This game is called Pong and was made popular in the 1970s by Atari Incorporated. A player may play against the computer as shown in this example. The player's 101 racket 565 is on the left half and the computer's racket 567 is on the right half of the game table 551. Ball 569 bounces off table sides 553, 555 but will go out the ends 575, 577. If ball 569 goes out the left end 575, a point goes to the computer. If ball 569 goes out the right end 577, a point goes to the player. The path of the ball 571 is shown bouncing off the player's paddle 565 and moving in the direction of the computer's half of the table. The net 573 separates the player's half on the left from the computer's half on the right. From the player's perspective on the left half, the paddle may move left 561 and right 563 based on the user's 101 control of the movement sensor inside wearable device 103.

Figure 7:
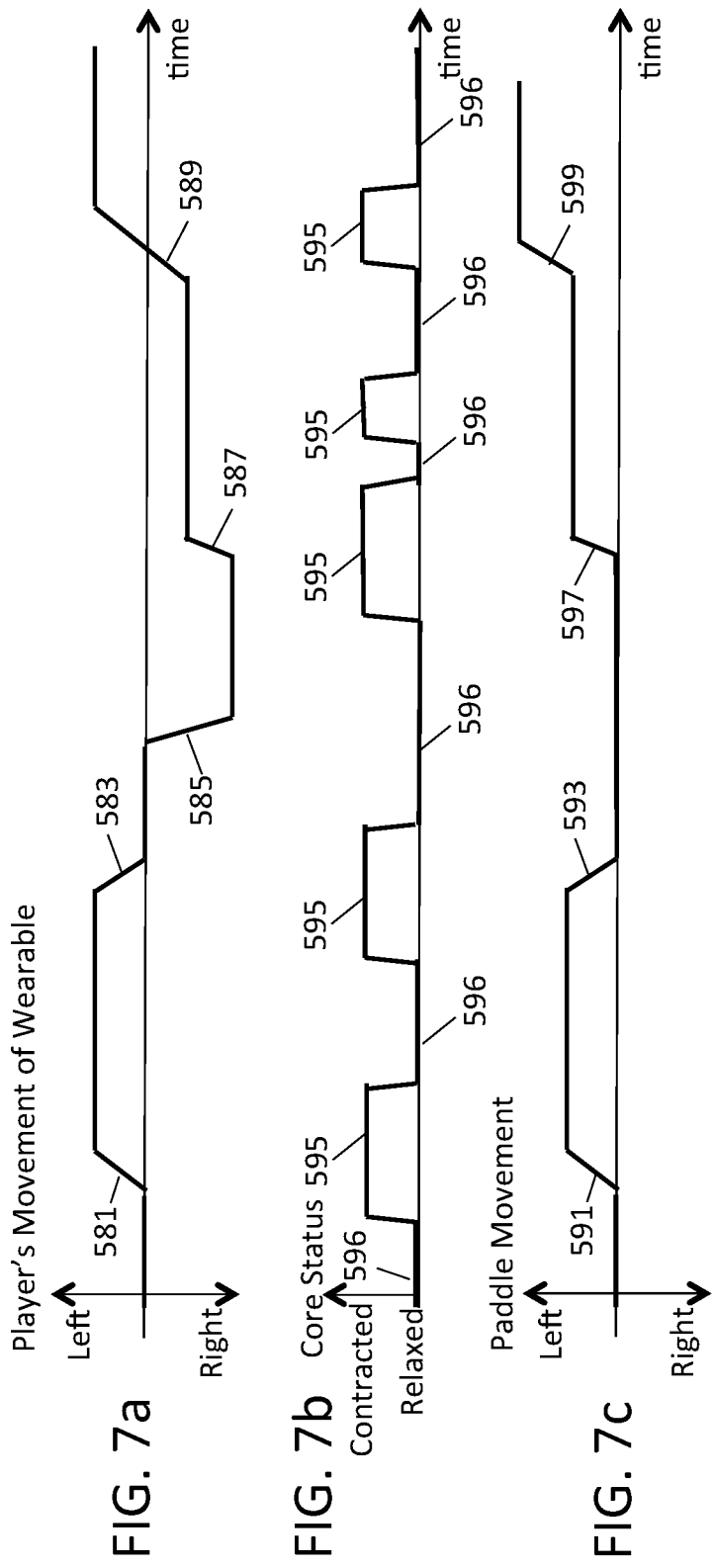
FIG. 7a illustrates an example graph of a player's movement versus time.
FIG. 7b illustrates an example graph of a player's core contraction versus time.
FIG. 7c illustrates an example graph of the resulting paddle movement in a ping pong game.

An embodiment of the system is now described. An example of a player's 101 movement resulting in movement of the wearable 103 in the left and right direction as a function of time is shown in FIG. 7*a*. An example of a player's 101 core status, whether contracted 595 or relaxed 596 as a function of time is shown in FIG. 7*b*. FIG. 7*c* shows the resulting paddle movement as a function of time using an embodiment of the Movement Criteria. Items in FIGS. 7*a*, 7*b*, and 7*c* are shown aligned in time.

Referring to FIG. 7*a*, the player first moves left 581 with core contracted 595 as shown in FIG. 7*b*. This meets Movement Criteria, resulting in paddle movement to the left 591. The core is then relaxed 596 and then contracted 595 again prior to a move back to the right 583. This again meets Movement Criteria, resulting in paddle movement back to the right 593. Next, the player moves right 585 but since core is still relaxed 596, Movement Criteria is not met and the Ramification 609 is a non-movement of the paddle.

Following this, left movement 587 occurs when core is contracted 595 and the paddle moves left 597. Core then relaxes 596, contracts 595, and relaxes 596 again. Since there is no player movement, there is no paddle movement. Finally, the player moves left 589 with core relaxed 596 so paddle does not move until core is contracted 595, resulting in a smaller paddle move left 599 than would have occurred had core been contracted throughout the move left 589. In another embodiment of the Movement Criteria, since the core is relaxed 596 at the start of movement left 589, the paddle may not move at all in response to movement left 589.

Figure 8:
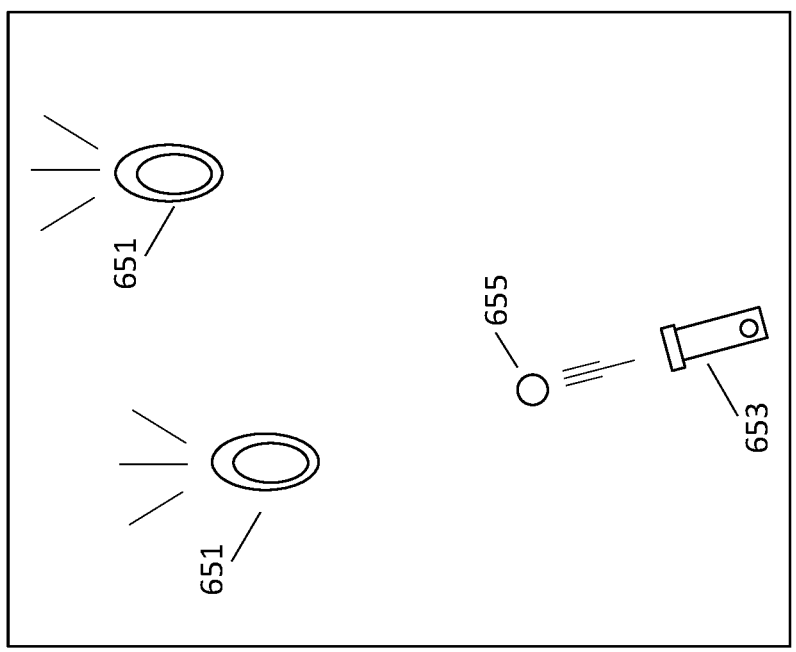
FIG. 8 illustrates a display for a video game with objects falling top to bottom and a shooting device that shoots balls at the objects.

Referring to FIG. 8, a visual from a basic shooter game is shown. Concentric ovals 651 enter from the top and move down to the bottom then out of the display. Centered at the bottom of the display is a shoot barrel 653 that shoots balls 655 in the direction the barrel is pointing. The player 101 controls the direction of the barrel 653 and controls when the balls 655 are shot from the barrel 653. In an embodiment, the direction of the barrel 652 is controlled by rotation of the player's 101 torso. In an embodiment, the barrel 653 rotates only when the player 101 engages the core muscles prior to the rotation. In another embodiment, a computer keyboard is used as a game interface 501. For some video game applications, the "a" key moves items left and the "d" key moves items right. In an application where the game is played on a computer, when the "a" key is pressed, the barrel 653 may rotate left and when the "d" key is pressed, the barrel 653 may rotate right. In an embodiment, the barrel 653 shoots a ball when the player 101 engages their core muscles. Each time the core muscles transition from relaxed to engaged, the transition is detected by the core contraction sensor on the wearable device 103 and a ball is fired. In an embodiment, the wearable device 103 communicates via a wireless link such as Bluetooth to the computer. A software driver may be used on the computer to interpret the data from the wearable device 103, and identify the transitions from a relaxed to engaged core and result in a ball 655 being shot from the barrel 653 in the video game.

Figure 9:
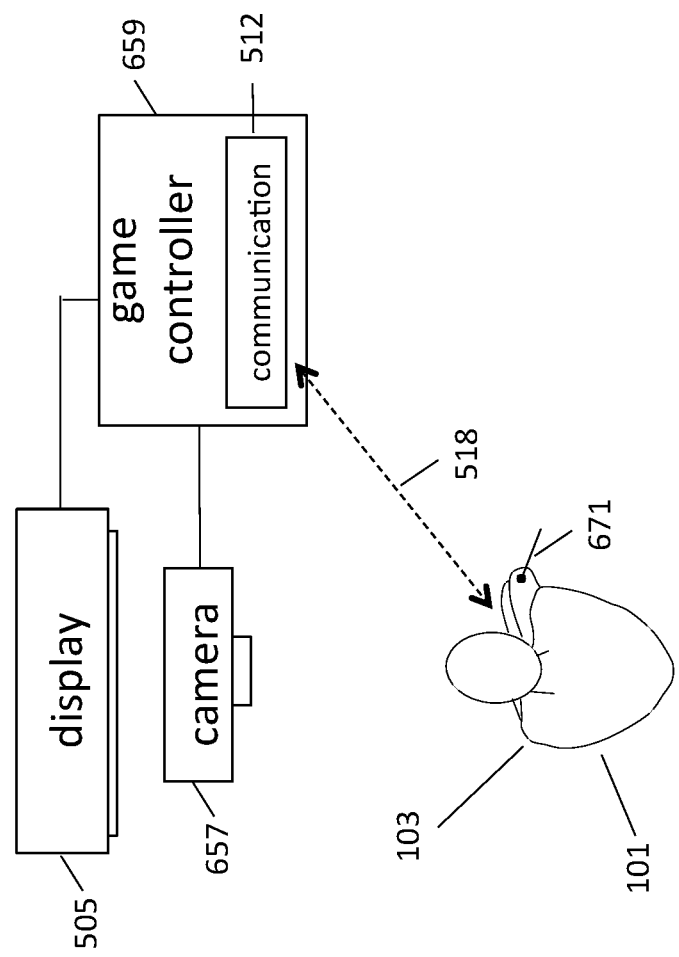
FIG. 9 illustrates an embodiment with a birds eye view of a player performing a golf backswing, a camera that tracks a player's body movement, the wearable device on the player's core, and a video game running on the game device that encourages engagement of the core coordinated with body movements with feedback provided through the video game.

Referring to FIG. 9, an embodiment with a system that generates a 3-D model of a player including a camera 657, game controller 659, and display 505 is shown. Wearable device 103 may be worn over the core muscles of player 101. The game controller 659 includes a communication block 512 to communicate with wearable device 103. In an embodiment, communication between the wearable device 103 and the communication block 512 in the game controller 659 over a wireless communication link 518. Game controller 659 takes data from the camera 657 and converts it into a 3-D model of the player in real-time. Digital signal processing techniques may be applied using the data from two or more cameras for identifying depth in order to build a 3-D model. In an embodiment with a real-time 3-D model of the player and real-time tracking of the core muscles, a video game to encourage contracting the core muscles coordinated with body movements may be implemented to develop muscle memory for athletic movements that can be practiced daily in the player's 101 home. In the example shown in FIG. 9, the player is practicing engaging the core muscles before a back swing in golf. The player may hold a stick 671 to mimic the feel of a golf club. By practicing this sequence of movements in the video game, a player may develop the habit to engage their core muscles prior to a golf back swing. Engaging the core muscles during a golf swing is one example of a movement that may benefit from support of the core muscles. Utilizing the video game may allow a player 101 to practice regularly at home and may facilitate the development of procedural memory, muscle memory, or neural patterning to help turn the practice of core engagement during a golf swing into a habit.

Figure 10:
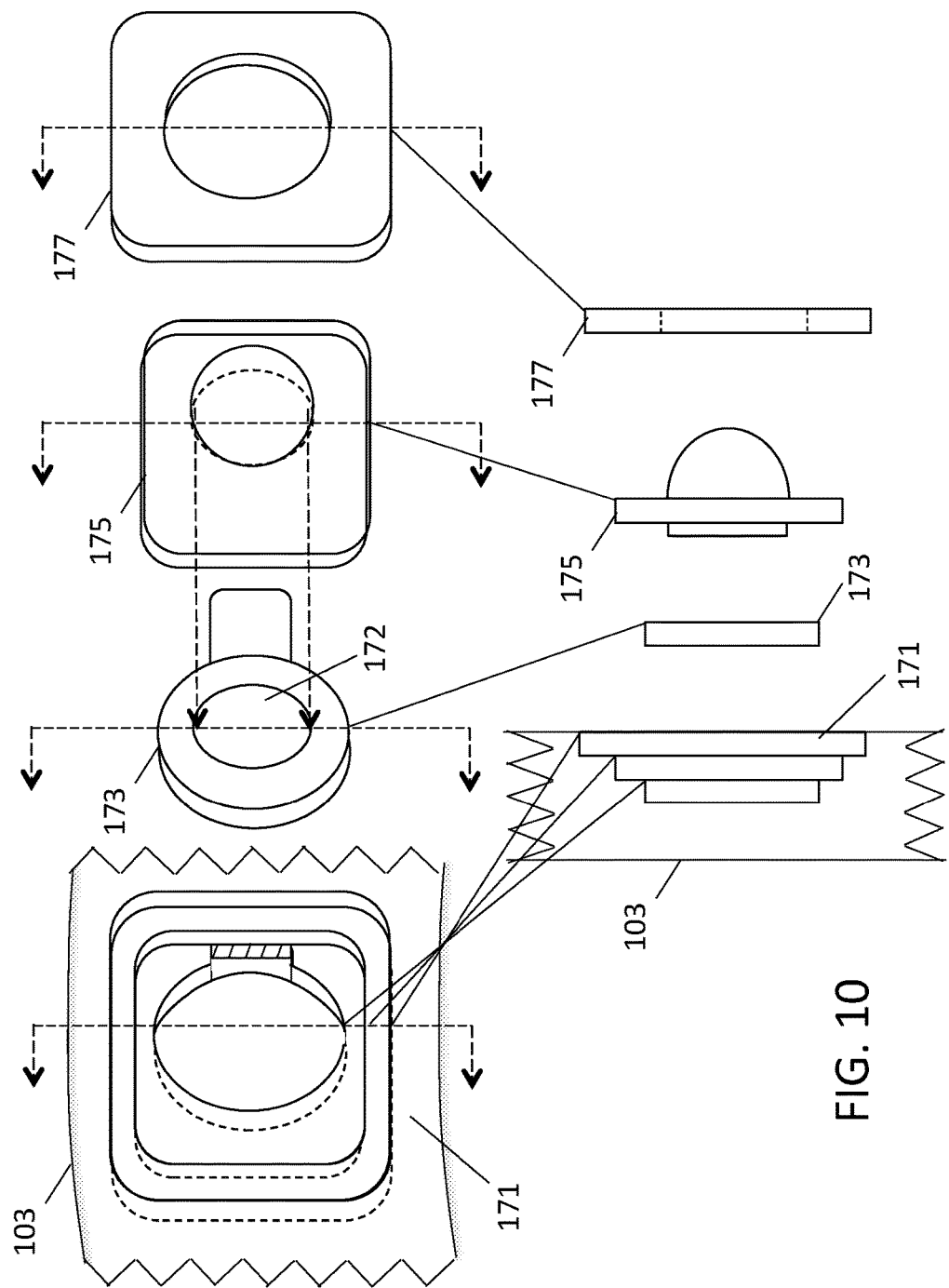
FIG. 10 illustrates an exploded view and a cross-sectional view of an embodiment of a core contraction sensor assembly.

In U.S. Pat. No. 9,226,706 and U.S. patent application Ser. Nos. 14/132,808, 14/789,136, 14/652,542, 14/817,964, 61/739,160, and 62/154,626, various approaches may be utilized to implement the core contraction sensor. FIG. 10 illustrates an exploded view of an embodiment utilizing a Force Sensing Resistor (FSR) 173 on the top of the figure while a cross-sectional view is shown at the bottom of the figure. Starting at the upper left and moving to the right, the exploded view includes the device 103 with volume removed 171 to custom fit a force sensing resistor 173 with active area 172, a bumper 175 that may be implemented with a rubber or rubber-like material with a brim, and a frame 177 that holds the force sensing resistor or FSR 173 and bumper 175 in place by holding the brim in place. The frame 177 may be attached to the device using glue or one or more screws or other attachment materials. Additional features may be designed into the brim of the bumper including an O-ring in order to promote water resistance in the design. In the cross-sectional view, the deepest cavity is where the FSR 173 may reside. Above the cavity for the FSR 173 is a cavity where the brim of the bumper 175 may reside. Above the bumper brim is a cavity to fit the frame 177 which attaches to the device body 103 to hold in place the FSR 173 and the bumper 175. Note in the cross-sectional view that the bumper 175 may have a small extrusion underneath it to interface to the active portion of the FSR 173. In an embodiment, the feature of the bumper 175 that interfaces to the user's 103 core may be shaped to achieve the objectives of comfort and sensitivity. In the example shown, the section of the bumper that will interface to the user's core is shown to be rounded. In an embodiment, the bumper may have a substantially flat area on the tip that interfaces to the user's core muscles while having a rounded top rim.

Referring to FIGS. 11*a*, an embodiment of an extender cap 181 may be added to the top of the bumper 175 to further extend the effective height and girth of the bumper 175. Referring to FIG. 11*b*, mushroom cap 193 is shown. Mushroom cap 193 is similar to extender cap with the feature that the area of the effective bumper against the body is increased while the height of the bumper is not appreciably increased or increased at all. The mushroom cap 193 may result in greater comfort to the user by reducing the apparent sharpness of the bumper against the users muscles. In an embodiment, a flat ring 191 may be placed around the bumper on the face of the wearable device. The ring 191 may keep the mushroom cap 193 from pressing down directly into the face of the wearable device 103 when pressure is placed on an outside edge of the mushroom cap 193, and reduce bending of the column region of the rubber bumper 175. In an embodiment, the ring 191 may be made from a firm pliable material such as felt, neoprene, or material with similar properties. In some applications, an extender feature may be added to the top of the mushroom cap 191 and bumper 175 in order to increase the height of the contraction sensor. In FIG. 11*c*, a view of the top portion of the rubber bumper is shown from an angle with mushroom cap 191 shown separated from the bumper. The mushroom cap 193 may be held in place via a snug fit or with an adhesive such as glue, double stick tape, or other adhesive.

Figure 12A:
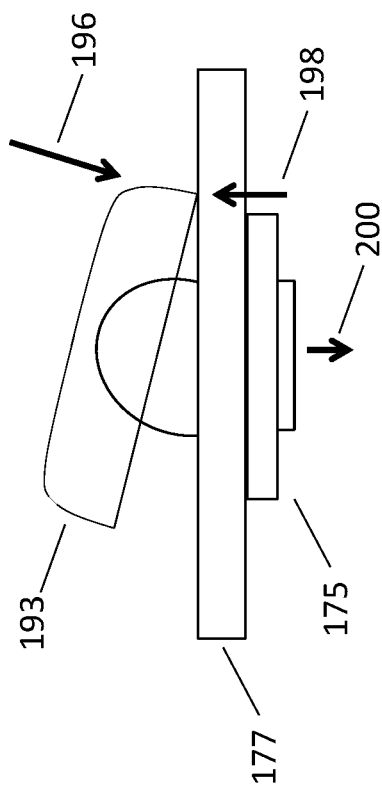
FIG. 12a illustrates bending of a bumper and extender cap when force is applied at an angle on an edge of the extender cap.

Referring to FIG. 12*a*, forces are indicated by arrows and an applied force 196 is shown applied to the right edge of mushroom cap 193. As a result, mushroom cap 193 presses against frame 177 resulting in a force 198 which opposes the downward component of force 196, and reduces force 200 against the FSR 173. While it is desirable to increase the girth of the mushroom cap 193 in order to have a larger area to couple to muscles, in many applications, the forces on the bumper 175 with the mushroom cap 193 may have one or more significant components that are not normal to the face of the device 103.

Figure 12B:
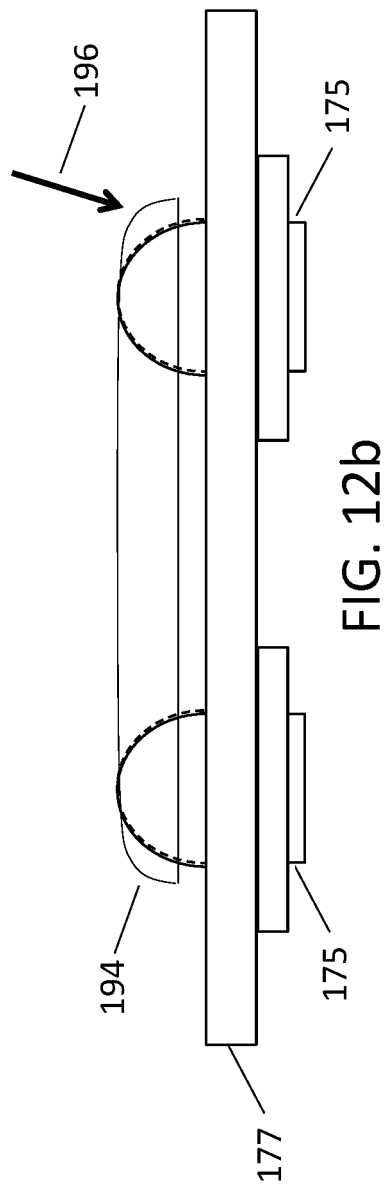
FIG. 12b illustrates a two bumper design with a unifier cap.

Referring to FIG. 12*b*, an embodiment with two bumpers 175 is shown with unifier cap 194. Unifier cap is similar to mushroom cap 193 as it increases the effective girth of the bumpers in order to provide a larger area to couple to the user's muscles. An important feature of the unifier cap 194 is that it may be designed so that even in the presence of forces not normal to the face of the device 103, the unifier cap 194 may not contact the frame 177 or the body of device 103.

In an embodiment, the height of the unifier cap 194 may be increased using unifier cap extender 621 as shown in FIG. 13*a*. An embodiment to attach unifier cap extender 621 to unifier cap 194 is shown in FIGS. 13*a* and 13*b* where clips 623 slide in through holes 625 that then hook onto the inside surface of unifier cap 194. Other approaches for attaching unifier cap extender 621 to unifier cap 194 may be utilized.

Referring to FIG. 14*a*, an embodiment with two bumpers 175 is shown. A Y-axis 615 and X-axis 613. Unifier cap 194 is shown surrounding both bumpers 175. In order to ensure unifier cap 194 does not contact the frame 177 or face of the device 103 when a force is applied at an angle of the edge of the unifier cap 194, unifier cap 194 is designed to be only slightly wider in the Y-dimension 615 as the bumper diameter. In FIG. 14*b*, an embodiment with three bumpers 175 is shown. Unifier cap 194 has larger size in the Y-dimension compared with the unifier cap 194 in the two bumper design. For some applications, the three bumper design is desirable since it results in a significant increase in the area of unifier cap 194.

In applications where two or more bumpers are used and FSRs are used as force sensors, separate FSRs may be used and placed beneath the bumpers and the outputs of the FSRs may be sensed independently. In another application, a custom FSR with multiple sensors placed beneath each bumper may be used. Electrically, each of the sensors in the multiple sensor FSR may be in parallel. Other configurations and FSR structures may be utilized. Optimizing the FSR shape and design with placement of the bumpers with similar shapes to optimally couple the FSR to the bumpers may be desirable for some applications.

In some applications, more than one wearable device may be simultaneously utilized. Multiple devices may allow more than one muscle to be monitored simultaneously. Multiple devices may allow the core muscles to be monitored in different positions simultaneously. The use of multiple wearable devices may reduce the likelihood of missing the detection of a core contraction or a muscle contraction. An embodiment employing two wearable devices 103 is shown in FIG. 15 where both devices are used to monitor the core muscles. In some applications, wireless standards common on some smart devices may support connection between an app running on the smart device to one wearable device at a time. In an embodiment, a first wearable device 103 establishes a wireless connection to smart device 503 over wireless link 518. Then, a second wearable device 103 may be connected via a wired link 520 to the first wearable device 103. In an embodiment, the wired link 520 may be a USB link. The second wearable device 103 may transmit via wired link 520 to the first wearable device 103. And the first wearable device 103 may transmit sensor data and derived data from both the first wearable device and the second wearable device to the smart device 503. In an embodiment, an app may run on smart device 503 and may communicate via audio and a display to the user, and may receive data from the first wearable device 103 and the second wearable device 103. Control data may be transmitted from the app running on smart device 503 via the wireless link 518 to the first wearable device 103 and the first device may transmit via wired link 520 the control data to the second wearable device 103.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Some embodiments of the invention are implemented as a program product for use with an embedded processor. The program(s) of the program product defines functions of the embodiments (including the methods described herein) and can be contained on a variety of signal-bearing media. Illustrative signal-bearing media include, but are not limited to: (i) information permanently stored on non-writable storage media; (ii) alterable information stored on writable storage media; and (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-accessible format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

The present invention and some of its advantages have been described in detail for some embodiments. It should be understood that although the process is described with reference to a device, system, and method for developing core contraction procedural memory, the process may be used in other contexts as well. It should also be understood that various changes, substitutions and alterations can be made herein without departing from the spirit and scope of the invention as defined by the appended claims. An embodiment of the invention may achieve multiple objectives, but not every embodiment falling within the scope of the attached claims will achieve every objective. Moreover, the scope of the present application is not intended to be limited to the particular embodiments of the process, machine, manufacture, composition of matter, means, methods and steps described in the specification. A person having ordinary skill in the art will readily appreciate from the disclosure of the present invention that processes, machines, manufacture, compositions of matter, means, methods, or steps, presently existing or later to be developed are equivalent to, and fall within the scope of, what is claimed. Accordingly, the appended claims are intended to include within their scope such processes, machines, manufacture, compositions of matter, means, methods, or steps.

What is claimed is:

1. A method for improvement of core muscles based support, comprising:
providing a core muscle contraction sensor, a movement sensor, a video game software program running on a processor, and a display in communication with the processor and a memory coupled to the processor;
detecting core contractions of the user with the core muscle contraction sensor;
transmitting core contraction signals from the core muscle contraction sensor to the processor;
detecting body movements of the user with the movement sensor;
transmitting body movement signals from the movement sensor to the processor;
determining by the processor that the body movement signals either indicate that a desired player movement has been performed or that the desired player movement has not been performed; and
converting by the video game program running on the processor, the desired player movements that have been performed which include the core contraction signals into video feedback signals that are output as positive actions of a visual object on a video game on the display and the desired player movements that have not been performed into the video feedback signals that are output as negative actions of the visual object on the video game on the display.

2. The method of claim 1 further comprising:
determining by the processor that the movement signals indicate a qualifying movement that benefits from the core contraction; and
converting by the video game program running on the processor, the movement signals that indicate the qualifying movement into qualifying movement video feedback signals that are output on the display.

3. The method of claim 2 further comprising:
detecting by the processor, a timing relationship between the qualifying movement and the core contraction signals;
identifying a protected qualifying movement when the core contraction signals occur throughout the qualifying movement; and
converting by the video game program running on the processor, the protected qualifying movement into protected qualifying movement video feedback signals.

4. The method of claim 3 further comprising:
detecting by the processor, a timing relationship between the qualifying movement and the core contraction signals;
identifying an unprotected qualifying movement when the core contraction signals does not occur throughout the qualifying movement; and
converting by the video game program running on the processor, the unprotected qualifying movement into unprotected qualifying movement video feedback signals.

5. The method of claim 4 wherein the protected qualifying movement video feedback signals are movements of an avatar in a first direction on the display.

6. The method of claim 5 wherein the unprotected qualifying movement video feedback signals are movements of the avatar in a second direction on the display.

7. The method of claim 5 wherein the unprotected qualifying movement video feedback signals are stopped movements of the avatar on the display.

8. A method for improvement of core muscles based support, comprising:
providing a contraction sensor, a movement sensor, a video game software program running on a processor, and a display in communication with the processor and a memory coupled to the processor;
displaying a video game scenario on the display with a movable object on the display;
detecting core contractions of the user with the contraction sensor; transmitting core contraction signals from the contraction sensor to the processor;
detecting body movements of the user with the movement sensor;
transmitting body movement signals from the movement sensor to the processor;
determining by the processor that the movement signals indicate a qualifying movement that benefits from the core contraction;
determining by the processor timing relationships between the core contraction signals and the body movement signals;
detecting by the processor, a timing relationship between the qualifying movement and the core contraction signals;
identifying by the processor, a protected qualifying movement when the core contraction signals occur during the qualifying movement and an unprotected qualifying movement when the core contraction signals does not occur during the qualifying movement; and
converting by the video game program running on the processor, the protected qualifying movement into a positive video feedback output signal when the core contraction signals occur throughout the qualifying movement that are output on the display; and
converting by the video game program running on the processor, the unprotected qualifying movement into a negative video feedback output signal that are output on the display.

9. The method of claim 8 wherein the positive video feedback output signal is translational or rotational movements of the movable object on the display.

10. The method of claim 8 wherein the negative video feedback output signal is a stopped movement of the movable object in the video game scenario on the display.

11. The method of claim 8 wherein the movable object is an avatar, the positive video feedback signal results in the avatar avoiding a hazard object in the video game scenario and the negative video feedback output signal results in the avatar colliding with the hazard object in the video game scenario.

12. The method of claim 8 wherein the positive video feedback signal results in the object moving faster in the video game scenario and the negative video feedback output signal results in the object moving slower in the video game scenario.

13. The method of claim 8 wherein the object is a the positive video feedback signal results in the object moving faster in the video game scenario and the negative video feedback output signal results in the object moving slower in the video game scenario.

14. A method for improvement of core muscles based support, comprising:
providing a wearable device having a contraction sensor, a movement sensor and a transmitter coupled to the contraction sensor and the movement sensor;
providing a computing device having a receiver in communication with the transmitter, a video game software program running on a processor, a display in communication with the processor and a memory coupled to the processor;
detecting core contractions of the user with the contraction sensor;
transmitting core contraction signals from the transmitter of the wearable device to the receiver of the computing device;
detecting body movements of the user with the movement sensor;
transmitting body movement signals from the transmitter of the wearable device to the receiver of the computing device;
determining by the processor that the body movement signals either indicate that a desired player movement has been performed or that the desired player movement has not been performed; and
converting by the video game program running on the processor, the desired player movements that have been performed which include the core contraction signals into video feedback signals that are output as positive actions of a visual object on a video game on the display and the desired player movements that have not been performed into the video feedback signals that are output as negative actions of the visual object on the video game on the display.

15. The method of claim 14 further comprising:
determining by the processor that the movement signals indicate a qualifying movement that benefits from the core contraction; and
converting by the video game program running on the processor, the movement signals that indicate the qualifying movement into qualifying movement video feedback signals that are output on the display.

16. The method of claim 15 further comprising:
detecting by the processor, a timing relationship between the qualifying movement and the core contraction signals;
identifying a protected qualifying movement when the core contraction signals occur throughout the qualifying movement; and
converting by the video game program running on the processor, the protected qualifying movement into protected qualifying movement video feedback signals.

17. The method of claim 16 further comprising:
detecting by the processor, a timing relationship between the qualifying movement and the core contraction signals;
identifying an unprotected qualifying movement when the core contraction signals does not occur throughout the qualifying movement; and
converting by the video game program running on the processor, the unprotected qualifying movement into unprotected qualifying movement video feedback signals.

18. The method of claim 17 wherein the protected qualifying movement video feedback signals are movements of an avatar in a first direction on the display.

19. The method of claim 18 wherein the unprotected qualifying movement video feedback signals are movements of the avatar in a second direction on the display.

20. The method of claim 18 wherein the unprotected qualifying movement video feedback signals are stopped movements of the avatar on the display.

* * * * *